United States Patent [19]

Schwartz

[11] 4,160,997
[45] Jul. 10, 1979

[54] INTRAORAL FLUOROSCOPE
[76] Inventor: Robert Schwartz, 1271 Westfield Ave., Rahway, N.J. 07065
[21] Appl. No.: 685,457
[22] Filed: May 12, 1976

Related U.S. Application Data

[63] Continuation-in-part of Ser. No. 469,655, May 14, 1974, abandoned.

[51] Int. Cl.$^2$ .................. H04N 7/18; H04N 5/32
[52] U.S. Cl. ........................... 358/93; 358/111
[58] Field of Search ............ 358/98, 93, 110, 111, 358/213, 106; 128/2 A, 4; 354/62, 63

[56] References Cited

U.S. PATENT DOCUMENTS

| | | | |
|---|---|---|---|
| 2,692,299 | 10/1954 | Longini | 358/111 |
| 3,051,166 | 8/1962 | Hovnanian | 128/4 |
| 3,495,084 | 2/1970 | Sheldon | 358/110 |

FOREIGN PATENT DOCUMENTS 604198  6/1948  United Kingdom ............... 358/111

OTHER PUBLICATIONS

Watson, Charge Coupling Technology Leads to Compact Video Cameras, Bell Labs Record, vol. 51, #9, Oct. 1973.

*Primary Examiner*—Richard Murray
*Assistant Examiner*—Michael A. Masinick

[57] ABSTRACT

An improved intraoral fluoroscope adapted for use with an electronic video display system is provided by the present invention. The preferred fluoroscope system comprises (a) a light transparent, phosphor-coated screen, (b) a visible light image conversion system for converting a visible light image to an electrical video signal output comprising one or more, and preferably a plurality, of charge coupled image sensors, the visible light image conversion system being in light communication with the light transparent, phosphor-coated screen, and (c) timing, control and transmission circuitry electrically connecting the light image conversion system to the video display system and adapted to receive and transmit the video signal output from the visible light image conversion system to the video display system.

5 Claims, 2 Drawing Figures

INTRAORAL FLUOROSCOPE

CROSS-REFERENCE TO RELATED APPLICATION

This application is a continuation-in-part of copending application Ser. No. 469,655, filed May 14, 1974 now abandoned.

BACKGROUND OF THE INVENTION

1. Field of the Invention

The present invention relates to an improved intraoral fluoroscope device. More particularly, the present invention is concerned with an improved intraoral fluoroscope device that is adapted for use with an electronic video display system.

2. Description of the Prior Art

The dental practitioner utilizes x-ray photographs as a basic diagnostic and operative tool. Conventionally, x-rays (or gamma and beta radiation emitted by radium) are directed through the tissue, bone or tooth structure being examined onto a film cartridge located directly opposite the energy source. Thereafter, the film is developed and the needed information secured from the resulting photograph. This conventional procedure suffers from many deficiencies. First of all, substantial delays are encountered when using conventional x-ray photography because of the necessity to await the development of the x-ray photographs and to retake photographs if the initial image secured is blurred. In situations where the patient is under sedation, such delays are obviously undesirable. Additionally, with conventional x-ray techniques, the patient must be subjected to a rather large dosage of x-ray energy in order to obtain an acceptable x-ray photograph. Typically, the radiated energy used must pass through varying depths of body tissue as well as the area for which x-ray photographs are sought. For many various reasons, it is desirable that the intensity of radiation used be diminished.

Alternates to the traditional x-ray system for obtaining pictures or images of internal body structures have been proposed in the prior art. Hovnanian, in U.S. Pat. No. 3,051,166 and in a publication entitled: "Fibre Optic Television Monitor and Fluoroscope," Proceedings of the Third International Conference on Medical Electronics, London, 1960, has described an endoscope which is inserted in the mouth and is employed for coverting x-rays into a visual image. Hovnanian's endoscope comprises a probe head that is coated with an image converting phosphor. The phosphor material converts an invisible radiant energy image into a visible light image which is transmitted through a fiber optic bundle to a television system which converts the light image transmitted by the fiber optic bundle into an enlarged visual image. The Hovnanian system suffers from many deficiencies. First of all, elaborate lens structures must be used to assist in the transmission and/or reception of light from the fiber optic bundle. Secondly, practical considerations limit the length of the fiber optic bundle that can be used and further the fiber elements of the bundle tend to fracture during fabrication and/or use which results in light transmission defects.

SUMMARY OF THE INVENTION

In accordance with the present invention, an intraoral fluoroscope adapted for use with an electronic video display system is provided. By the present invention, x-ray type pictures can be secured instantaneously without the picture distortions inherent in a fiber optic system. Two related intraoral (mouth insertable) systems may be used. The first intraoral fluoroscope system comprises (a) a sensing means for converting an invisible radiant energy image, derived from an x-ray source, a radium source, etc., into a visible light image; (b) a visible light image conversion system for converting a visible light image into an electrical video signal output comprising at least one charge coupled image sensor, the image conversion system being in direct visible light communication with and in close physical proximity to the sensing means; and (c) timing, control and transmission means that serve to electrically connect the conversion system and a video display system and which is adapted to receive and transmit the video signal output from the visible light image conversion system to the video display system. Desirably, the sensing means comprises a non-lens (both lateral surfaces being planar) screen member having a conventional image-converting phosphor material deposited thereon. The second system comprises (a) a non-lens (both lateral surfaces being planar), x-ray transparent screen member; (b) an x-ray image conversion system for converting an x-ray image into an electrical video signal output comprising at least one charge coupled image sensor, the image conversion system being in direct x-ray communication and in close physical proximity to the screen member; and (c) timing, control and transmission means that serve to electrically connect the conversion system and a video display system and which is adapted to receive and transmit the video signal output from the x-ray image conversion system to the video display system. Preferably, the visible light image conversion system used in either system comprises an array of charge coupled image sensors packaged together using hybrid chip and wire or beam lead techniques. The expressions "direct visible light communication" or "direct x-ray communication" are intended to require that a lens or lens system not be interposed between the sensing means or screen member, as applicable, and the conversion system.

BRIEF DESCRIPTION OF THE DRAWINGS

The invention will be better understood by reference to the accompanying drawings in which.

Figure 1:
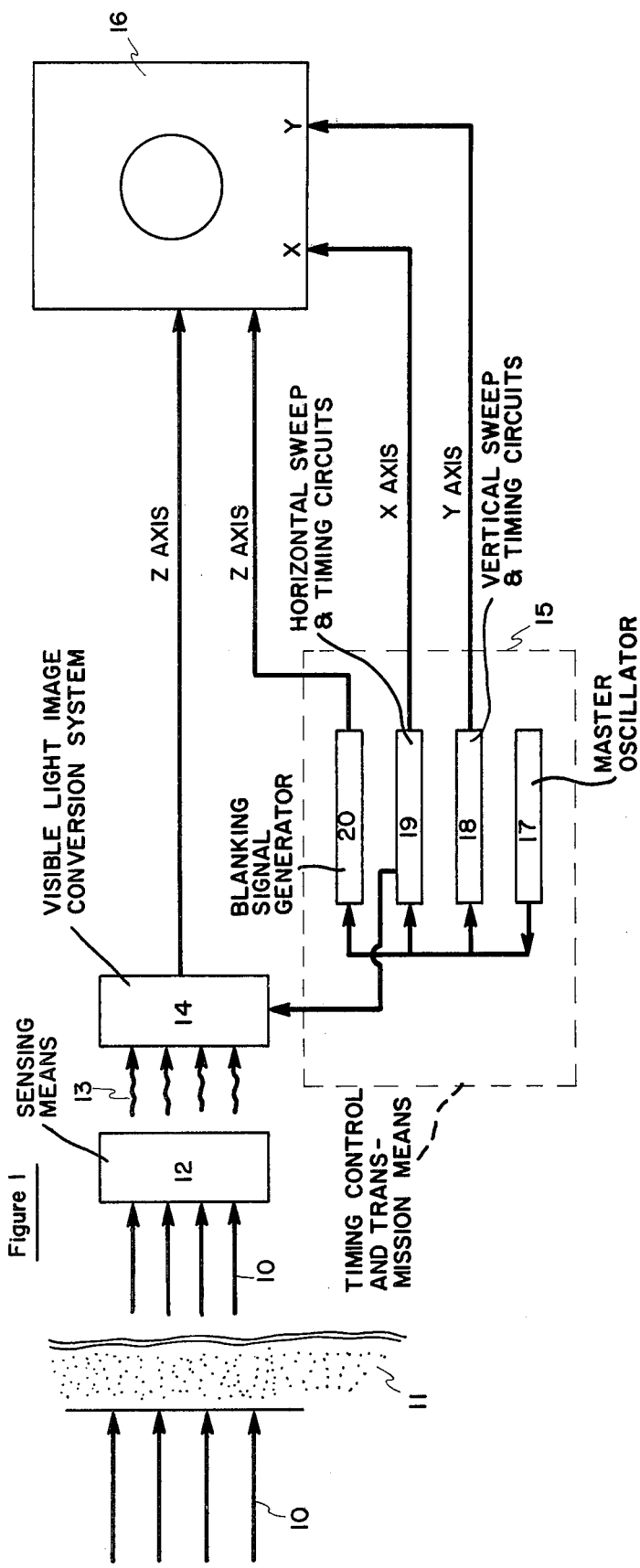
FIG. 1 is a schematic representation of the preferred intraoral fluoroscope embodiment of the present invention.

The preferred intraoral fluoroscope of the present invention is adapted to be used in conjunction with an electronic video display system such as an oscilloscope or television display. The fluoroscope serves to convert instantaneously radiated energy images, such as x-ray images, into a typical electronic video display. In use, the intraoral fluoroscope is located at the point immediately adjacent to the area sought to be examined. Thereafter, x-rays are applied to the outside surface of the body and directed toward the sensing means of the fluoroscope system. As noted above, the preferred intraoral fluoroscope system serves to convert the resulting x-ray image into a visible light image which in turn is converted to an electrical video signal output which is subsequently transmitted and converted into a video display.

Turning now to the figures, the preferred intraoral fluoroscope comprises a sensing means 12, a visible light image conversion system 14, and timing, control and transmission means 15. The visual signal output from image conversion system 14 with proper timing and control functions, is transmitted to an electronic video display system 16, preferably a CRT oscilloscope.

Sensing means 12 consists of a screen member, preferably a non-lens screen member, having a conventional phosphor material deposited thereon which acts to convert x-rays into visible light. If the phosphor is located on the outside surface of the screen member (not immediately adjacent to system 14), the screen member should be visible light transparent. If the phosphor is located immediately adjacent to system 14, the screen member should be x-ray transparent. Useful phosphor materials include cadmium sulfide, zinc sulfide, and zinc cadmium sulfide. Barium platinocyanide can be used to convert gamma and beta ray images into visible light images. In the less preferred system, a non-lens, x-ray transparent screen member, which can be fabricated from appropriate polymeric materials, is used rather than the sensing means of the preferred embodiment.

The visible light image conversion system 14 comprises at least one charge coupled image sensor which serves to convert a visible light image into an electrical video signal output. The charge coupled sensor senses and retains photon generated electrical charges in depletion regions formed by a MOS-type capacitor and transfers the signal from each element of the sensor (charge pocket) through a plurality of potential wells to a detector-preamplifier. An example of a useful charge coupled image sensor is the solid state self-scanning image sensor CCD 201 manufactured by the Fairchild Semiconductor Components Group, Fairchild Camera and Instrument Corporation. Information concerning CCD 201 can be found in Fairchild Semiconductor Data Sheet 20006-11-0018-093 5M (October 1973) and Data Sheet 2006-11-0023-123 7.5M (January 1974), the disclosures of which are herein incorporated by reference. Additional information regarding the use of charge coupled image sensors can be found in a collection of technical papers entitled "Imaging With Charge Transfer Devices" presented at the March 26–29, 1974 meetings of the Institute of Electrical and Electronics Engineers International Convention and Exposition. Similar charge coupled devices may be used as the x-ray image conversion system for the less preferred embodiment. The charge coupled image sensors described herein are believed to be capable of converting x-ray images directly into an electrical video signal output.

Figure 2:
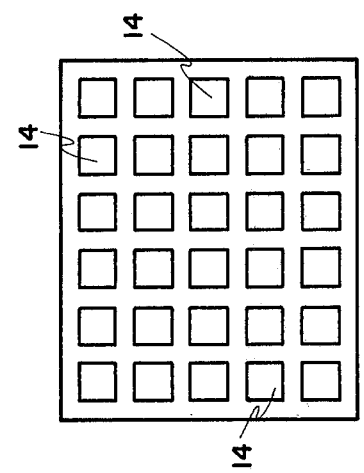
FIG. 2 is a schematic representation of an array of charge coupled image sensors.

A plurality of charge coupled image sensors are desirably employed in either the preferred or less preferred systems in order to obtain a large picture area. Preferably, the charge coupled image sensors are arranged in a matrix as shown in FIG. 2. Each CCD 201 device consists of (a) 10,000 image sensors in a 100×100 array; (b) 100 columns of 2-phase vertical analog shift registers inter-digitated with the image sensor array; (c) a 102 element, 2-phase horizontal analog output shift register that is charge coupled to the output of each of the 100 columns shift registers; (d) a gated charge detector output preamplifier which detects and converts the charges delivered from the image sensor array to a video output voltage; and (e) a compensation output amplifier that provides capability for differential amplification and noise suppression.

In the use of the preferred embodiment of this invention, radiated energy such as x-rays 10 are applied to the portion of the mouth 11 being examined and passed therethrough and impinge upon sensing means 12 which is located inside the mouth. Sensing means 12 preferably comprises a light transparent screen member having a phosphor material deposited on the outside surface thereof. The phosphor materials serve to convert the x-rays into visible light 13 which passes through sensing means 12 and impinges upon the charge coupled visible light image sensor 14. The charge coupled image sensor 14 is in direct visible light communication with the sensing means. Preferably, the sensing means 12 is located immediately adjacent to the charge coupled image sensors. When light in the visible range is incident on the charge coupled image sensor, electrons are generated in each of the image sensors of the array. Electrical clocking of the photogate, 2-phase vertical shift registers delivers the electrical charge from each element of the array to the gated charge detector preamplifier which provides a video signal output. The video signal output is amplitude modulated and is applied to the Z axis of a CRT oscilloscope 16 and will intensity modulate the video display. Timing, control and transmission means 15 consist of suitable circuitry that develop timing signals to control the charge coupled device and provide X and Y axis drive for the CRT oscilloscope 16. The result is a video display that is analogous to an x-ray photograph.

In more detail, timing, control and transmission means 15 for either the preferred or less preferred embodiments of this invention may consist of master oscillator 17, vertical sweep and timing circuits 18 that provide Y axis drive for the oscilloscope vertical sweep, horizontal sweep and timing circuits 19 that provide X axis drive for the oscilloscope horizontal sweep, and blanking signal generator 20 that provides blanking signals to the oscilloscope Z axis. The horizontal sweep and timing circuits 19 also are adapted to provide timing and drive voltages to sensor 14. While a CRT oscilloscope is the preferred electronic video display system, it should be recognized that a television system may also be used. When a television system is used, specific art recognized timing and control waveforms must be applied to the television receiver to meet the requirements of a standard 525-line television system.

Sensing means 12 and the visible light image conversion system 14 of the preferred embodiment and the x-ray transparent screen member and x-ray image conversion system of the less preferred embodiment are encased within a protective covering, which is transparent to invisible radiant energy, and are adapted to be inserted in the human mouth. Any of the usual synthetic thermoplastic or thermosetting compositions may be employed. The intraoral fluoroscope systems of the present invention can be employed as an operative or diagnostic tool. As noted previously, the present device enables the practitioner to obtain instantaneously x-ray quality pictures. Furthermore, high quality photographs can be obtained with reduced radiation exposure levels because of the possibility of electrically storing the video signal output from the visible light image conversion system or x-ray image conversion system, as applicable, on magnetic tape as in a conventional video tape recorder.

What is claimed is:

1. An intraoral fluoroscope adapted for use with an electronic video display system comprising:
    (a) sensing means for converting an invisible radiant energy image to a visible light image;

(b) a light image conversion system for converting a visible light image to an electrical video signal output comprising at least one charge coupled image sensor, said image conversion system being in visible light communication with said sensing means and said light image conversion system and sensing means adapted for insertion into the human mouth; and (c) timing, control and transmission means electrically connecting said conversion system and said video display system and adapted to receive and transmit said video signal output from said conversion system to said video display system.

2. The fluoroscope of claim 1 wherein said sensing means comprises a screen member, a phosphor material for converting an invisible radiant energy image to a visible light image deposited thereon.

3. The fluoroscope of claim 2, wherein said sensing means is in direct visible light communication with and in close physical proximity to said light image conversion system.

4. The intraoral fluoroscope of claim 1 wherein said visible light image conversion system comprises a plurality of electrically interconnected charge coupled image sensors.

5. An intraoral fluoroscope adapted for use with an electronic video display system comprising:

(a) a non-lens, x-ray transparent screen member;

(b) an x-ray image conversion system for converting an x-ray image into an electrical video signal output comprising at least one charge coupled image sensor, the image conversion system being in direct x-ray communication with and in close physical proximity to the said screen member and said x-ray image conversion system and screen member adapted for insertion into the human mouth; and (c) timing, control and transmission means electrically connecting said conversion system and said video display system and adapted to receive and transmit said video signal output from said conversion system to said video display system.

* * * * *